United States Patent
Nishito (12)

(10) Patent No.: US 6,434,771 B1
(45) Date of Patent: Aug. 20, 2002

(54) MATTRESS INCORPORATING TOURMALINE

(75) Inventor: Akira Nishito, Kotabe (JP)

(73) Assignee: F & H USA, Inc., Tustin, CA (US)

( * ) Notice: Subject to any disclaimer, the term of this patent is extended or adjusted under 35 U.S.C. 154(b) by 28 days.

(21) Appl. No.: 09/416,589

(22) Filed: Oct. 12, 1999

(51) Int. Cl.[7] .............................................. A47C 27/22
(52) U.S. Cl. ....................... 5/693; 5/736; 5/901; 5/906
(58) Field of Search ........................... 5/693, 736, 731, 5/901, 906

(56) References Cited

U.S. PATENT DOCUMENTS

| | | | | |
|---|---|---|---|---|
| 4,509,219 A | * | 4/1985 | Yagi ........................... | 5/906 X |
| 4,680,822 A | | 7/1987 | Fujino | |
| 5,035,017 A | * | 7/1991 | Komuro .................... | 5/906 X |
| 5,601,909 A | * | 2/1997 | Kubo ......................... | 442/417 |
| 5,744,222 A | * | 4/1998 | Sugihara .................... | 428/196 |

OTHER PUBLICATIONS

BRITANNICA.COM, Tourmaline, Encyclopaedia Britannica Article, Website: www.Britannica.com.
MINERALS.NET, Tourmaline Group, Article from www.minerals.net website.
MINERALS.NET, Chemicals Formula of Tourmaline, Article from www. minerals.net website.
MINERALS.NET, Silicates, Article from www. minerals.net website.
MINERALS.NET, Cyclosilicates, Article from www. minerals.net website.

* cited by examiner

Primary Examiner—Lynne H. Browne
Assistant Examiner—Fredrick Conley
(74) Attorney, Agent, or Firm—Trojan Law Offices

(57) ABSTRACT

The present invention is a mattress that has tourmaline discs attached to the mattress. The mattress is an egg-crate mattress which has at least two different elevations, an upper elevation and a lower elevation. The mattress is made-up of foam. The tourmaline discs are attached to the mattress with glue in a plurality of the lower elevations of the egg-crate mattress. The mattress can also have magnets attached in a plurality of the lower elevations.

15 Claims, 2 Drawing Sheets

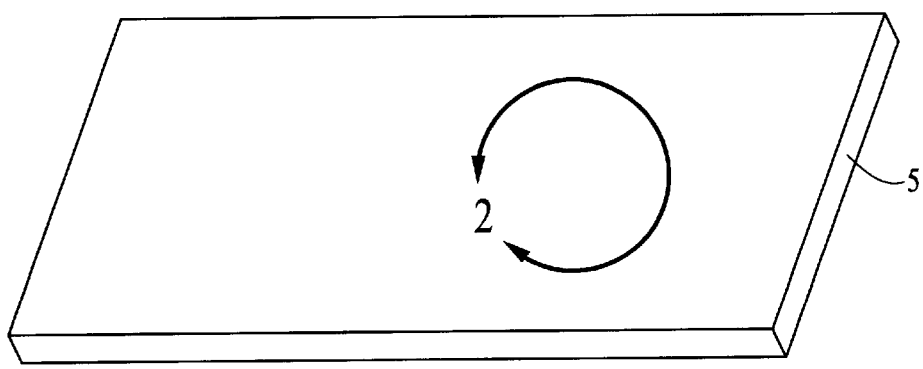
*fig.1*
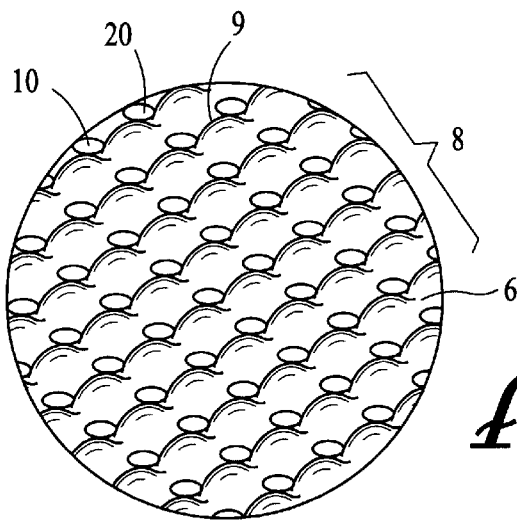
*fig.2*
*fig.3*
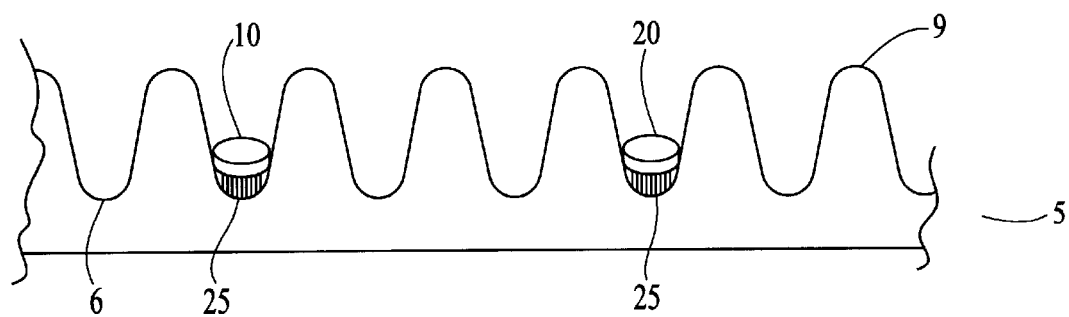

MATTRESS INCORPORATING TOURMALINE

BACKGROUND OF THE INVENTION

1. Field of the Invention

The invention relates generally to mattresses and more specifically to mattresses incorporating tourmaline.

2. Description of Related Art

Many different kinds of mattresses have been developed over the years in order to improve the comfort of mattresses for improving the quality of sleep of the user. For example, water beds, air beds and beds with pillows covering them, are all beds currently on the market. It is evident from the wide range of beds available that there is always room for improvement in the art.

SUMMARY OF THE INVENTION

The present invention introduces such improvement. In a first embodiment the invention includes a mattress and tourmaline attached to the mattress. It is preferred that the invention also include at least one magnet attached to the mattress. It is also preferred that the tourmaline be in the form of a disc. Having the tourmaline be in the shape of a disc allows the tourmaline to come into contact with a user of the mattress without having the contact be uncomfortable for the user. The discs are attached to the mattress with an adhesive substance. Further preferred is that the mattress has a plurality of depressions and that the tourmaline discs are attached in the depressions. It is also preferred that the mattress be made of foam which has an egg-crate shape. The tourmaline discs may be in the form of a composite material that contains tourmaline such as that sold by Nippon Magnetics USA, Inc. of Los Angeles Calif. A composite material may be preferred because of its strenth and durability.

The second preferred embodiment of the invention includes an egg-crate shaped mattress pad which has a multiplicity of upper and lower elevations, and the tourmaline is attached to the mattress in at least one of the lower elevations. It is preferred that the invention include at least one magnet attached to the mattress in the lower elevation. It is also preferred that the mattress be made of foam. It is further preferred that the tourmaline be glued to the mattress.

The usefulness and benefits of tourmaline have been shown in the many studies conducted on tourmaline. Tourmaline produces negative ions, purifies the air and water, is an effective sterilizer, and produces infra-red light. The infra-red light generates heat and when the tourmaline is combined with other sources of heat, the tourmalines generation of heat is increased. Thus attaching it to a mattress, where the other source of heat will be body heat, the tourmaline will generate even more heat than without the external source of heat, therefore, keeping the user of the tourmaline mattress warmer than without the use of tourmaline. Also, the infra-red light production stimulates blood circulation in capillary vessels which also keeps the user of the tourmaline mattress warm.

The generation of heat by the tourmaline is another benefit which will help the user to sleep better. Maintaining constant body temperature during sleep is important for increasing the quality and duration of sleep for the user. As a result of tourmaline's heat generation, combining it with a mattress will in turn heat the user of the mattress and thus give the user a good warm nights rest.

Another benefit of the combination of a mattress and tourmaline is that people believe that tourmaline provides positive health effects. Therefore, the invention gives the user piece of mind when they lay down to sleep. The piece of mind provided by the invention will help the user sleep better than if they did not have piece of mind. As such, the invention is useful in aiding users who have trouble sleeping.

The tourmaline produces negatively charged ions, these ions transforms the body's pH from acidic to basic. As a result of the production of negative ions, the use of tourmaline has four major effects on the body. The first major effect is that it helps regulate the nervous system. The second major effect is that the negative ions promote cell tissue growth. The third major effect is purification of the blood. The fourth major effect resulting from the production of the negative ions is that it strengthens the immune system.

Further, adding magnets to the invention creates a synergistic effect when used with the tourmaline. Thus including them in the invention increases the positive benefits that derived from the use of the invention.

All of the foregoing operational principles and advantages of the present invention will be more fully appreciated upon consideration of the following detailed description, with reference to the appended drawings.

BRIEF DESCRIPTION OF THE DRAWINGS

FIG. 1 is a perspective view of the mattress;

FIG. 2 is a close-up view of a portion of the egg-crate shaped mattress;

FIG. 3 is an isometric view from the side of the egg-crate mattress having the peaks and valleys, and having the tourmaline disc and magnet attached to the mattress in the valleys;

DESCRIPTION OF THE PREFERRED EMBODIMENTS

Figure 4:
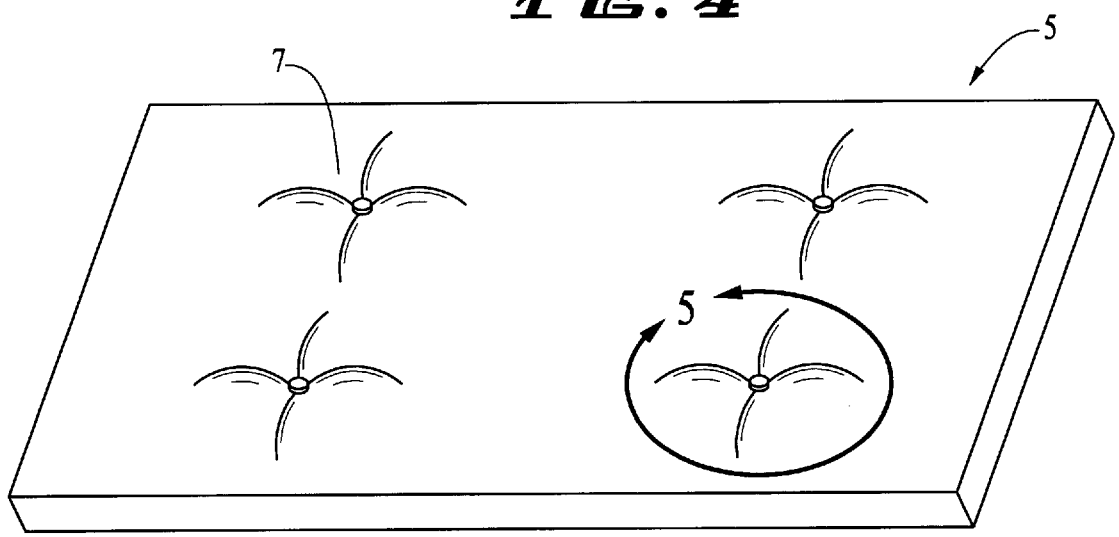
FIG. 4 is a perspective view of an alternative embodiment of the invention of a mattress having depressions with tourmaline discs in the depressions.
Figure 5:
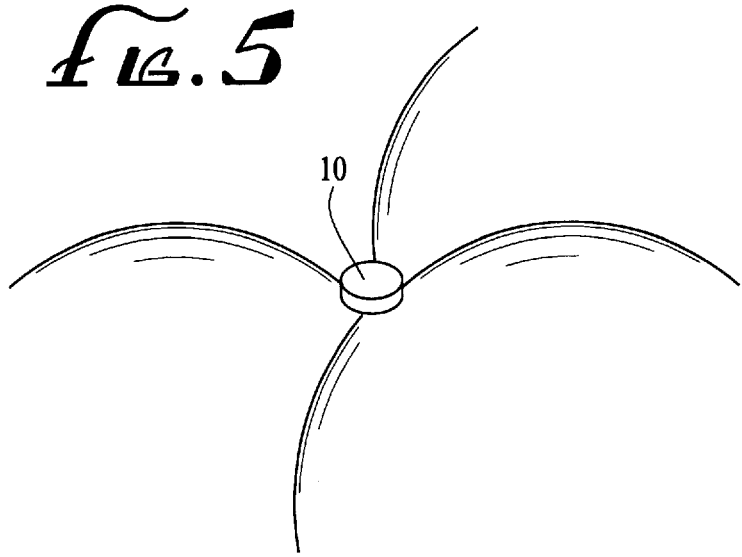
FIG. 5 is a close-up view of a portion of the mattress showing the tourmaline disc in the depression of the mattress.

While the invention will be described in connection with preferred embodiments, it will be understood that it is not intended to limit the invention to those embodiments. On the contrary, it is intended to cover all alternatives, modifications, and equivalents as may be included within the spirit and scope of the invention as defined by the appended claims.

The present invention includes a mattress 5 (FIG. 1). The mattress can be made-up of foam, cotton, or any other material suitable for use as a mattress. The mattress can also be an egg-crate mattress 8 having upper elevations 9 and lower elevations 6 (FIGS. 2 and 3). Within the lower elevations of the egg-crate mattress, tourmaline discs 10 can be attached to the mattress with any suitable adhesive substance 25. The discs can also be attached to the mattress by any other suitable method for ensuring that the discs stay in contact with the mattress so that the combination of the mattress and tourmaline are effective, such as, having the discs enclosed in a netting and having the netting attached to the mattress or the discs can be attached by drilling holes in the discs and sewing them to the mattress as if they were buttons. The magnets 20 can also be attached to the mattress in a similar manner by using an adhesive substance 25 or any other suitable method such as the netting described above.

In an alternative embodiment the invention includes a mattress 5 having at least one depression 7 (FIG. 4). Within the depression a tourmaline disc 10 can be attached to the mattress. Attaching the disc in a depression or lower elevation increases the level of comfort for the user of the mattress. The discs can be rigid and therefore unnecessarily irritate the user of the mattress if the discs are not lower than the top plane of the mattress. Further, having the tourmaline in the shape of a disc also increases the level of comfort for the user of the mattress combined with tourmaline.

I claim:

1. A mattress device comprising:

tourmaline, which is disc shaped and contained within a composite material;

at least one magnet; and a mattress comprising at least one pad having a contact surface with a first elevation and a second elevation; and said tourmaline and said at least one magnet are fixedly attached to the second elevation.

2. The mattress device of claim 1, wherein the mattress is comprised of foam.

3. The mattress device of claim 1, wherein said at least one pad has an egg-crate shape.

4. The mattress device of claim 1, wherein said tourmaline and said at least one magnet are fixedly attached to the second elevation with an adhesive.

5. A mattress device comprising:

tourmaline;

at least one magnet;

a mattress comprising at least one pad having a contact surface with a first elevation and a second elevation; and said tourmaline and said at least one magnet are fixedly attached to the second elevation.

6. The mattress device of claim 5, wherein the tourmaline is disc shaped and fixedly attached to the contact surface of the mattress with an adhesive substance.

7. The mattress device of claim 6, wherein the contact surface of the mattress has a plurality of depressions, and at least one tourmaline disc is attached in at least one of the depressions.

8. The mattress device of claim 5, wherein the mattress is comprised of foam.

9. The mattress device of claim 5, wherein the tourmaline is contained within a composite material.

10. A mattress device comprising:

tourmaline; and a mattress comprising at least one pad having a contact surface with a first elevation and a second elevation; and said tourmaline is fixedly attached to the second elevation.

11. The mattress device of claim 10, further comprising at least one magnet fixedly attached to the second elevation.

12. The mattress device of claim 10, wherein the tourmaline is disc shaped and fixedly attached to the second elevation of the contact surface with an adhesive.

13. The mattress device of claim 10, wherein the mattress is comprised of foam.

14. The mattress device of claim 10, wherein said at least one pad has an egg-crate shape.

15. The mattress device of claim 10, wherein said tourmaline is contained within a composite material.

\* \* \* \* \*